United States Patent
Ito

(10) Patent No.: US 10,732,401 B2
(45) Date of Patent: Aug. 4, 2020

(54) OPTICAL UNIT HAVING MOVABLE BODY AND VOICE COIL MOTOR FOR MOVING LENS GROUP AND ENDOSCOPE HAVING OPTICAL UNIT

(71) Applicant: OLYMPUS CORPORATION, Tokyo (JP)

(72) Inventor: Tadashi Ito, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 374 days.

(21) Appl. No.: 15/823,757

(22) Filed: Nov. 28, 2017

(65) Prior Publication Data

US 2018/0081164 A1     Mar. 22, 2018

Related U.S. Application Data

(63) Continuation of application No. PCT/JP2015/065876, filed on Jun. 2, 2015.

(51) Int. Cl.
*G02B 23/24* (2006.01)
*A61B 1/00* (2006.01)
(Continued)

(52) U.S. Cl.
CPC ...... *G02B 23/2438* (2013.01); *A61B 1/00002* (2013.01); *A61B 1/00188* (2013.01);
(Continued)

(58) Field of Classification Search
CPC ............ A61B 1/00163; A61B 1/00188; A61B 1/00096; G02B 23/2438; G02B 7/04;
(Continued)

(56) References Cited

U.S. PATENT DOCUMENTS 7,262,927 B1 * 8/2007 Shyu ...................... G02B 7/026
359/694
7,940,482 B2    5/2011 Sato
(Continued)

FOREIGN PATENT DOCUMENTS

CN        2840086 Y       11/2006
JP        2006276565 A    10/2006
(Continued)

OTHER PUBLICATIONS

Chinese Office Action dated Jul. 15, 2019 in Chinese Patent Application No. 201580080546.5.
(Continued)

*Primary Examiner* — John P Leubecker
(74) *Attorney, Agent, or Firm* — Scully, Scott, Murphy & Presser, P.C.

(57) ABSTRACT

An optical unit includes: a fixing part including a front frame portion, a rear frame portion, and a fixing part main body; a movable part arranged slidably relative to the fixing part main body; and a voice coil motor including a magnetic portion, and a coil arranged at the fixing part main body and positioned on a radially outer side of the fixing part main body with respect to the magnetic portion, the voice coil motor being capable of moving the movable part relative to the fixing part main body along a direction of the optical axis. A maximum dimension of the fixing part main body in a first direction parallel to a magnetization direction of the magnetic portion is greater than a maximum dimension of the fixing part main body in a second direction perpendicular to the first direction and the direction of the optical axis.

17 Claims, 10 Drawing Sheets

(51) Int. Cl.
  *H02K 41/035* (2006.01)
  *G02B 7/10* (2006.01)
  *G02B 7/08* (2006.01)
  *G02B 23/26* (2006.01)
(52) U.S. Cl.
  CPC ............... *G02B 7/08* (2013.01); *G02B 7/102* (2013.01); *H02K 41/0356* (2013.01); *A61B 1/00096* (2013.01); *G02B 23/26* (2013.01)
(58) Field of Classification Search
  CPC ........ G02B 7/08; G02B 7/09; H02K 41/0354; H02K 41/0356
  See application file for complete search history.

(56) References Cited

U.S. PATENT DOCUMENTS

| | | |
|---|---|---|
| 9,448,397 B2 | 9/2016 | Makiyama et al. |
| 2006/0214520 A1* | 9/2006 | Tseng ........................ G02B 7/02 310/14 |
| 2010/0246035 A1* | 9/2010 | Yamashita ............. G02B 7/023 359/824 |
| 2011/0210690 A1* | 9/2011 | Vogel .................. G02B 23/2476 318/631 |
| 2012/0002102 A1* | 1/2012 | Sekimoto ............... G02B 7/022 348/374 |
| 2013/0193778 A1* | 8/2013 | Wieters .............. G02B 23/2407 310/12.04 |
| 2013/0314517 A1* | 11/2013 | Makiyama ............. A61B 1/045 348/65 |
| 2015/0282692 A1* | 10/2015 | Wieters .............. A61B 1/00068 604/95.05 |
| 2015/0340939 A1* | 11/2015 | Kelp ................... H02K 41/0356 310/12.19 |
| 2016/0374543 A1* | 12/2016 | Wieters .............. A61B 1/00071 600/167 |

FOREIGN PATENT DOCUMENTS

| | | | |
|---|---|---|---|
| JP | 2007041616 A | 2/2007 | |
| JP | 5031666 B2 | 9/2012 | |
| WO | WO 2014156267 A1 * | 10/2014 | ............... G02B 7/04 |
| WO | 2014203626 A1 | 12/2014 | |

OTHER PUBLICATIONS

International Search Report dated Aug. 25, 2015 issued in PCT/JP2015/065876.
English Abstract of Japanese Publication No. 2009-288385 A, dated Oct. 12, 2009.

* cited by examiner ical unit according to the first embodiment. FIG. 2 is an exploded perspective view illustrating the configuration of the optical unit according to the first embodiment. FIG. 3 is a cross-sectional view illustrating a configuration of main parts of the optical unit according to the first embodiment. FIG. 4 is a cross-sectional view of the optical unit, at a cross-section taken along a line I-I in FIG. 3. Additionally, FIG. 3 is also a cross-sectional view of the optical unit, at a cross-section taken along a line II-II in FIG. 4.

OPTICAL UNIT HAVING MOVABLE BODY AND VOICE COIL MOTOR FOR MOVING LENS GROUP AND ENDOSCOPE HAVING OPTICAL UNIT

CROSS-REFERENCE TO RELATED APPLICATION

This application is a continuation of International Application No. PCT/JP2015/065876, filed on Jun. 2, 2015, the entire contents of which are incorporated herein by reference.

BACKGROUND

The present disclosure relates to an optical unit and an endoscope.

In the related art, there is disclosed a technique of using an electromagnetic actuator, i.e., a voice coil motor, which includes a movable lens frame provided with a movable lens group, and which uses a coil and a magnet to realize a zoom function for changing the shooting magnification by moving the movable lens frame forward or backward and a focus function of adjusting the focus by moving the movable lens frame forward or backward (for example, see JP 5031666 B1). The zoom function and the focus function are provided to an endoscope including an insertion unit to be inserted into a subject, for example.

SUMMARY

An optical unit may include: a fixing part including a front frame portion configured to hold an object-side fixed lens group, a rear frame portion configured to hold an image-side fixed lens group or an image sensor, and a fixing part main body configured to hold the front frame portion and the rear frame portion; a movable part configured to hold a movable lens group between the object-side fixed lens group and the image-side fixed lens group or the image sensor, the movable part being arranged, slidably relative to the fixing part main body, on a radially inner side of the fixing part main body; and a voice coil motor including a magnetic portion arranged at the movable part and magnetically polarized in a direction intersecting an optical axis of the object-side fixed lens group, and a coil arranged at the fixing part main body and positioned on a radially outer side of a magnet, the voice coil motor being capable of moving the movable part relative to the fixing part main body along a direction of the optical axis, wherein a maximum dimension of the fixing part main body in a first direction parallel to a magnetization direction of the magnetic portion is greater than a maximum dimension of the fixing part main body in a second direction perpendicular to the first direction and the direction of the optical axis.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, modes for carrying out the present disclosure (hereinafter referred to as "embodiment(s)") will be described.

First Embodiment

Figure 1:
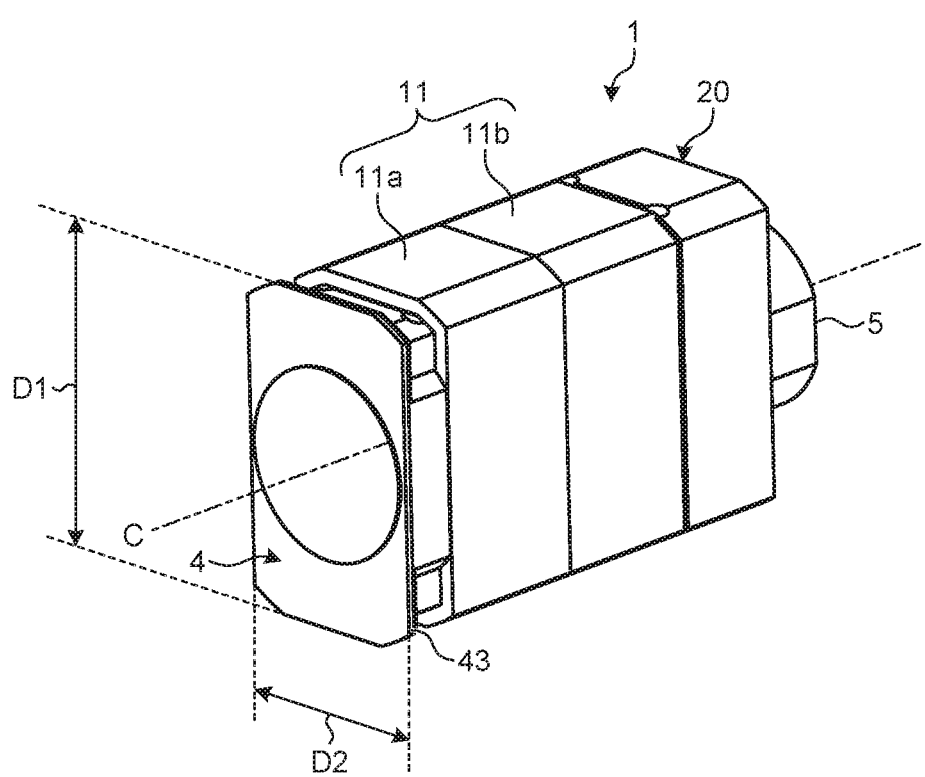
FIG. 1 is a perspective view illustrating a configuration of an optical unit according to a first embodiment.
Figure 2:
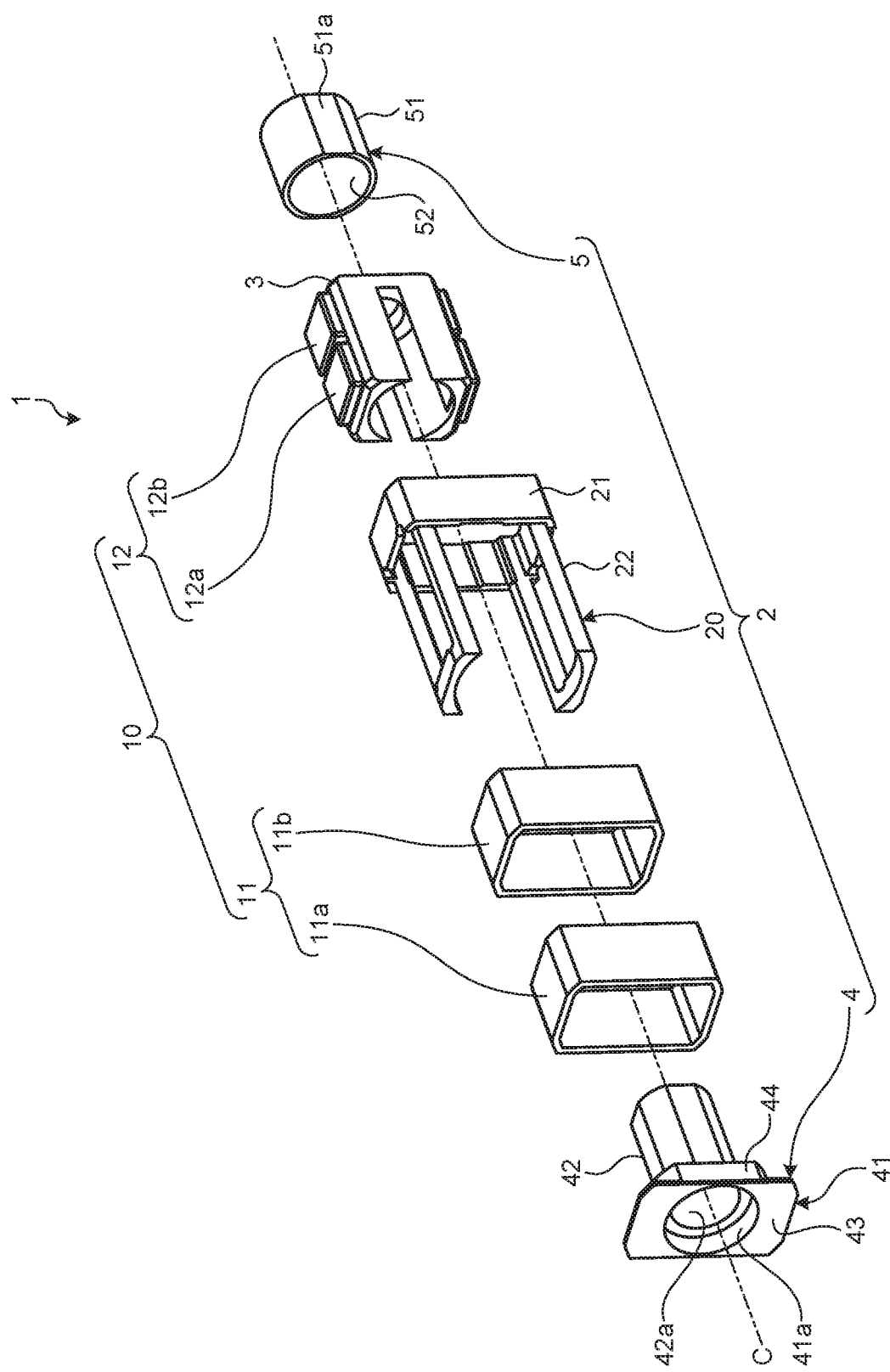
FIG. 2 is an exploded perspective view illustrating the configuration of the optical unit according to the first embodiment.
Figure 3:
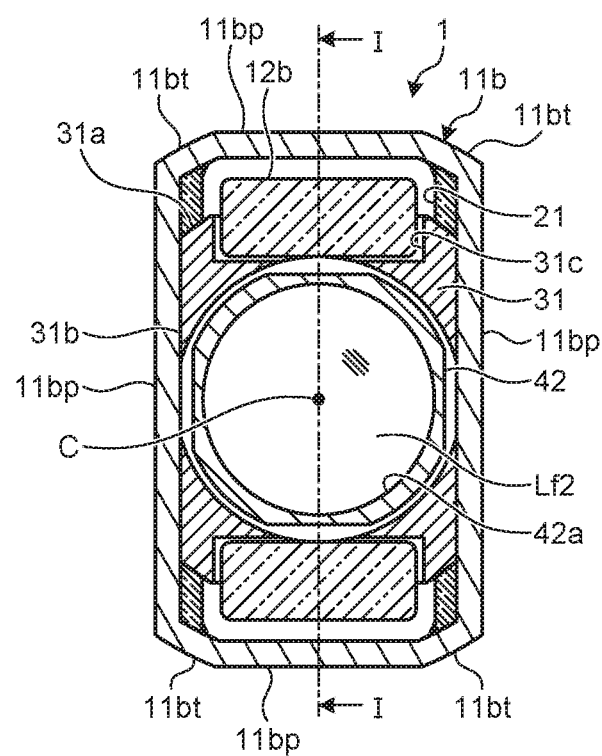
FIG. 3 is a cross-sectional view illustrating a configuration of main parts of the optical unit according to the first embodiment.
Figure 4:
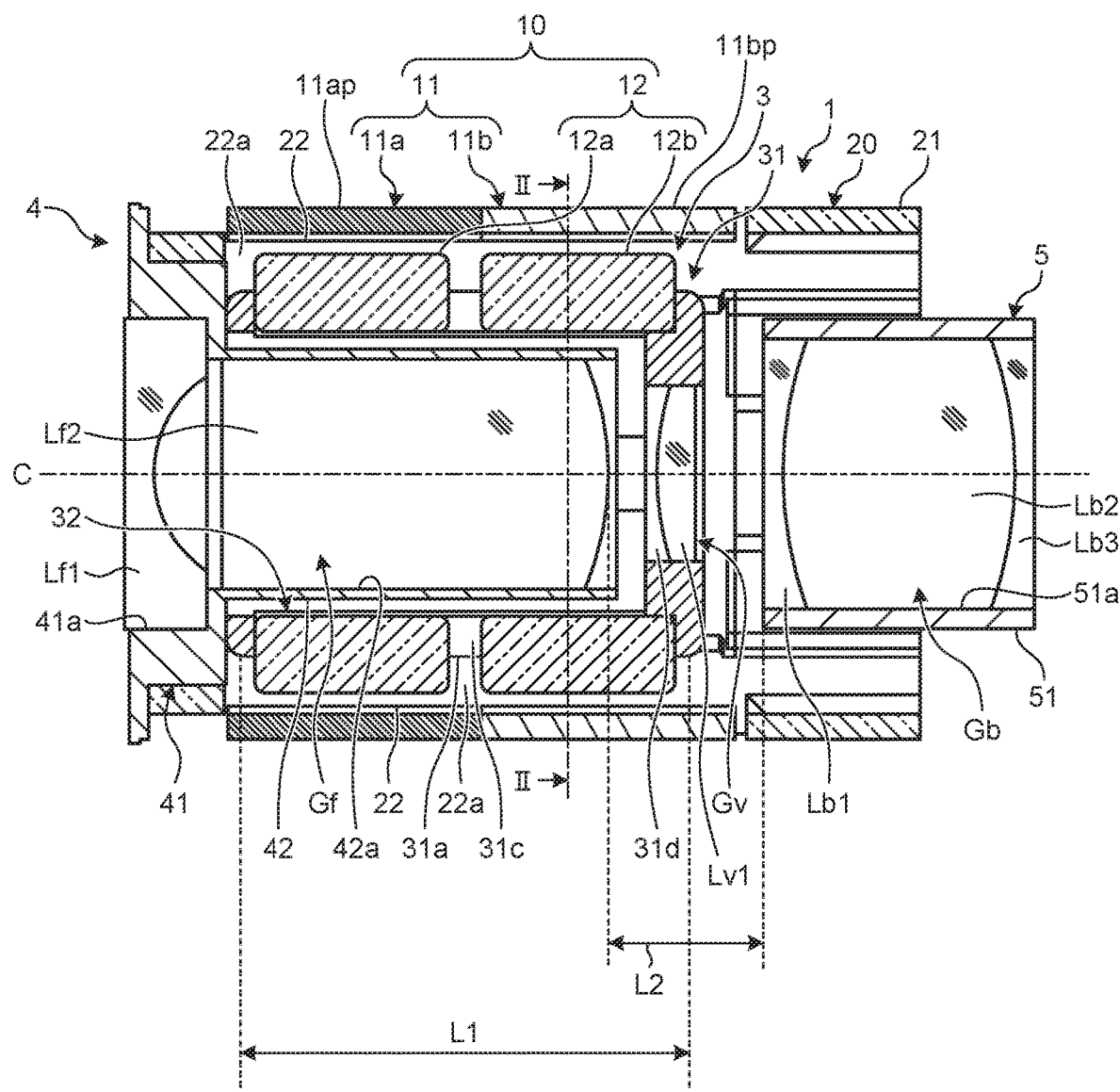
FIG. 4 is a cross-sectional view of the optical unit, at a cross-section taken along a line I-I in FIG. 3.

FIG. 1 is a perspective view illustrating a configuration of an optical unit according to a first embodiment. FIG. 2 is an exploded perspective view illustrating the configuration of the optical unit according to the first embodiment. FIG. 3 is a cross-sectional view illustrating a configuration of main parts of the optical unit according to the first embodiment. FIG. 4 is a cross-sectional view of the optical unit, at a cross-section taken along a line I-I in FIG. 3. Additionally, FIG. 3 is also a cross-sectional view of the optical unit, at a cross-section taken along a line II-II in FIG. 4.

An optical unit 1 illustrated in FIGS. 1 to 4 includes a fixing part 2, a movable part 3 capable of moving relative to the fixing part 2, and a voice coil motor 10 for generating a driving force for moving the movable part 3 relative to the fixing part 2. In the following, one side in an axis C direction will be referred to as an object side, and the other side opposite the object side will be referred to as an image side. In the present specification, the axis C is described to be coincident with an optical axis of the optical unit 1.

The fixing part 2 includes a fixing part main body 20, a front frame portion 4 for holding an object-side fixed lens group Gf, which is on the object side than a movable lens group Gv held by the movable part 3, the front frame portion 4 being attached to the object side of the fixing part main body 20, and a rear frame portion 5 for holding an image-side fixed lens group Gb, which is on the image side than the movable lens group Gv, the rear frame portion 5 being attached to the image side of the fixing part main body 20.

Figure 5:
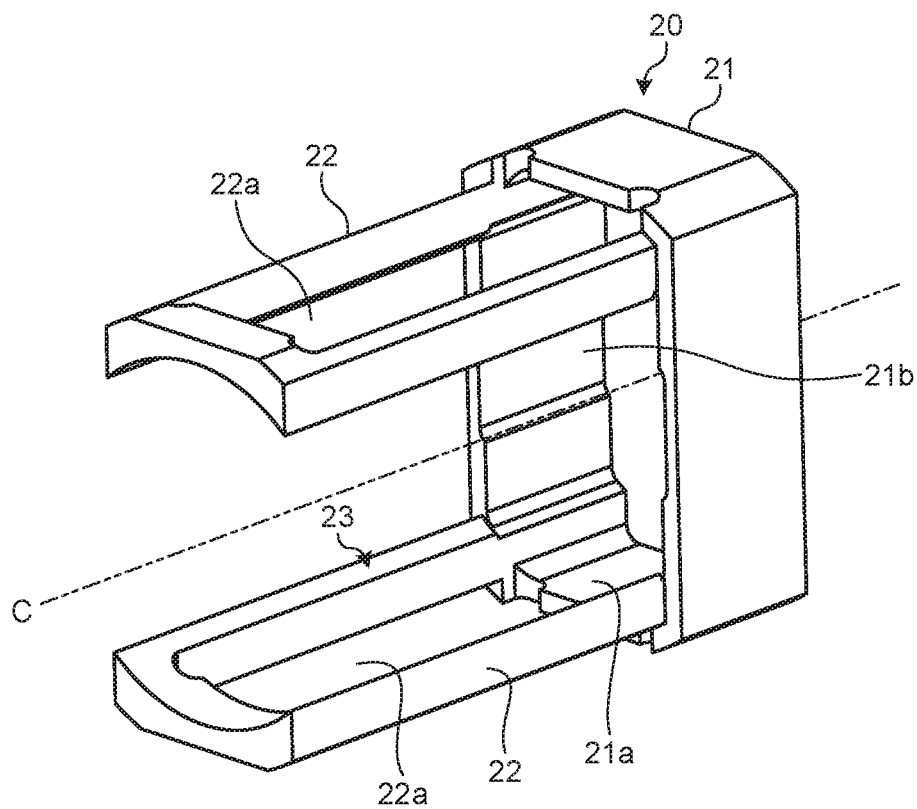
FIG. 5 is a perspective view illustrating a configuration of a fixing part main body of the optical unit according to the first embodiment.

FIG. 5 is a perspective view illustrating a configuration of the fixing part main body 20. The fixing part main body 20 illustrated in the drawing is formed from a cylindrical member having a predetermined axis C at the center. The fixing part main body 20 has an oval shape when seen in a plan view from the axis C direction, and has a cylindrical shape which is substantially symmetric with respect to a plane that passes through the axis C and that is parallel to the axis C. The fixing part main body 20 includes a cylindrical portion 21, which is cylindrical with the axis C as the center axis, and support portions 22 for supporting a coil 11 (see FIG. 1 and the like) of the voice coil motor 10, the support portions 22 extending from the cylindrical portion 21, toward the object side and along the axis C direction. In the following, a plane that passes through the axis C will refer to a plane that passes through the axis C and that is parallel to the axis C. The oval shape mentioned above is a shape that is octagonal when seen in a plan view from the C axis direction like the fixing part main body 20, with four corners of a rectangle being C-chamfered. Additionally, the "oval shape" in the present specification includes, in addition to the shape having four corners C-chamfered, a rectangular shape having four corners R-chamfered, a shape having arc portions and linear portions when seen in a plan view from the axis C direction, like the rear frame portion 5 described below, and the like, and refers to a shape according to which dimensions in two directions are different on a plane perpendicular to the axis C direction, as described below, the two directions being a magnetization direction of the voice coil motor 10 and a direction perpendicular to the magnetization direction. Also, the fixing part main body 20 desirably has a cylindrical shape which is symmetric with respect to the plane that passes through the axis C and that is parallel to the axis C, but does not have to be perfectly symmetric, and the radii of the R-chamfered corners may be different.

A projection shape of the cylindrical portion 21 in the axis C direction (the shape of the outer circumference and the shape of the inner circumference) is oval. The cylindrical portion 21 is formed protruding radially outward than the support portions 22. A groove 21a is formed on a fixing-side sliding surface 23 on the radially inner side of the cylindrical portion 21. At the time of attachment of the movable part 3, a magnet 12, described below, passes through the groove 21a. The movable part 3 may thereby be smoothly attached to the fixing part main body 20. Additionally, the cylindrical portion 21 may be formed separately from the support portions 22, and may be attached to the support portions 22 at the time of assembly.

Lightening portions 22a are formed to the support portions 22 by partially hollowing the support portions 22. Specifically, two lightening portions 22a penetrating the support portions 22 in the radial direction are formed at positions facing each other with respect to the axis C (center axis) in the longitudinal direction of the support portions 22. Radially inner sides of the support portions 22 other than the lightening portions 22a have an arc-shaped elliptical shape, and are made fixing-side sliding surfaces 23 for guiding and supporting the movable part 3. The fixing-side sliding surfaces 23 have a shape that is divided in a circumferential direction by the lightening portions 22a. Moreover, the radially inner sides of the support portions 22 other than the lightening portions 22a may be plane or curved with different radii along the circumferential direction, instead of being spherical.

A projection shape of the front frame portion 4 in the axis C direction is oval, and the front frame portion 4 has a cylindrical shape which is substantially symmetric with respect to the plane that is parallel to the axis C. The front frame portion 4 is a stepped cylindrical member including a distal end portion 41 and a proximal end portion 42. The distal end portion 41 includes a first distal end portion 43 having an aperture, an outer edge of an object-side distal end surface of the first distal end portion 43 having substantially the same oval shape as the outer edge of the cylindrical portion 21, and a cylindrical second distal end portion 44 extending in the axis C direction from the first distal end portion 43. The proximal end portion 42 has a cylindrical shape extending from the second distal end portion 44. An inner circumferential surface 41a of the distal end portion 41 forms a stepped hollow space, with a greater diameter on the object side. Additionally, the center axis of the front frame portion 4 is referred to as the axis C in FIG. 2 and the like, because the center axis coincides with the center axis of the fixing part main body 20 at the time of attachment. Also, the front frame portion 4 desirably has a cylindrical shape which is symmetric with respect to the plane that is parallel to the axis C, but does not have to be perfectly symmetric.

The front frame portion 4 holds the object-side fixed lens group Gf. The object-side fixed lens group Gf includes a first front lens Lf1 and a second front lens Lf2, and the lenses are arranged in this order from the object side. The inner circumferential surface 41a of the distal end portion 41 holds the first front lens Lf1, and an inner circumferential portion 42a of the proximal end portion 42 holds the second front lens Lf2.

At the time of inserting the front frame portion 4 into the fixing part main body 20, insertion is performed by fitting the second distal end portion 44 into an object-side distal end portions of the support portions 22 of the fixing part main body 20, and the first distal end portion 43 is caused to abut against the distal ends of the support portions 22 of the fixing part main body 20.

The rear frame portion 5 is a cylindrical member which has an oval shape when seen in a plan view from the axis C direction, and which includes an outer circumferential portion 51 and an inner circumferential portion 52. The outer circumferential portion 51 includes cut-out portions 51a for fitting with the fixing part main body 20. The rear frame portion 5 has a cylindrical shape which is substantially symmetric with respect to the plane that passes through the axis C. Additionally, as in the case of the front frame portion 4, the center axis of the rear frame portion 5 is referred to as the axis C, because the center axis coincides with the center axis of the fixing part main body 20 at the time of attachment. Also, the rear frame portion 5 desirably has a cylindrical shape which is symmetric with respect to the plane that passes through the axis C, but does not have to be perfectly symmetric.

The rear frame portion 5 holds the image-side fixed lens group Gb. The image-side fixed lens group Gb includes a first rear lens Lb1, a second rear lens Lb2, and a third rear lens Lb3. The inner circumferential portion 52 holds the first rear lens Lb1, the second rear lens Lb2, and the third rear lens Lb3 in this order from the object side. At the time of inserting the rear frame portion 5 into the fixing part main body 20, insertion is performed by fitting the cut-out portions 51a with side portions 21b of the fixing-side sliding surfaces 23 of the cylindrical portion 21.

The fixing part 2 having the configuration described above is formed from a non-magnetic material, for example. Such materials may include an austenitic stainless steel having a magnetic permeability greater than 1.0, aluminum, and resin, among non-magnetic materials.

Figure 6:
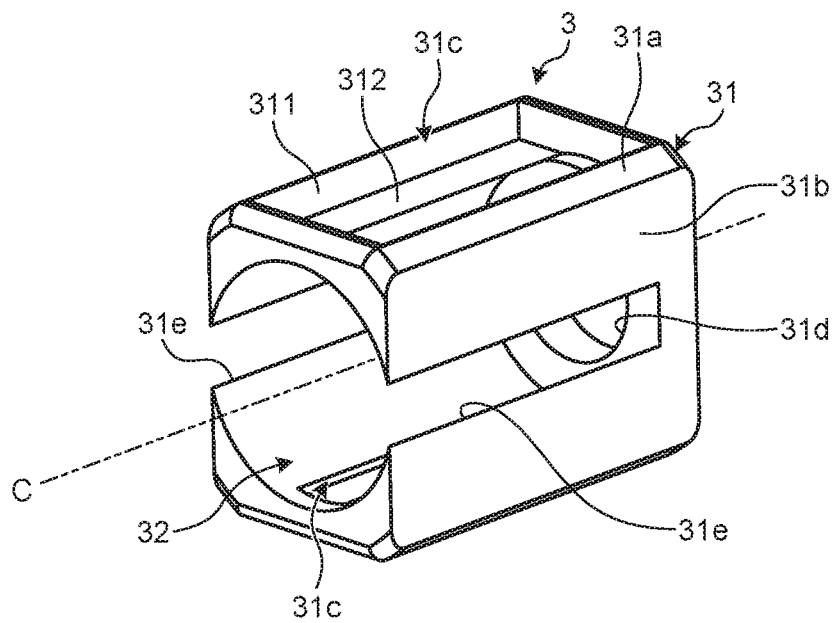
FIG. 6 is a perspective view illustrating a configuration of a movable part of the optical unit according to the first embodiment.

FIG. 6 is a perspective view illustrating a configuration of the movable part 3. The movable part 3 illustrated in the drawing is formed as a cylindrical member including an outer circumferential portion 31 and an inner circumferential portion 32, where one side of the cylindrical member is bottomed. In the following, the center axis of the movable part 3 will also be referred to as the axis C. This is because the center axis of the movable part 3 and the center axis of the fixing part main body 20 coincide with each other at the time of attachment.

A projection shape of the outer circumferential portion 31 in the axis C direction is oval, and the outer circumferential portion 31 includes movable-side sliding surfaces 31a, which are outer circumferential surfaces that contact the fixing part main body 20, and planar portions 31b, which are continuous to the movable-side sliding surfaces 31a. In the case illustrated in FIG. 6, the movable part 3 includes, along directions perpendicular to the normal lines of the planar portions 31b, two lightening portions 31c penetrating in the radial direction. Also, the movable part 3 includes an aperture portion 31d provided at one surface (a bottom portion of the cylindrical shape which is bottomed on one side) in the axis C direction, the aperture portion 31d forming a part of the inner circumferential portion 32, and cut-out portions 31e formed by cutting out parts of the respective movable-side sliding surfaces 31a along the axis C direction.

The lightening portion 31c includes side portions 311 continuous to the movable-side sliding surfaces 31a of the outer circumferential portion 31, and bottom portions 312 provided on the side of the inner circumferential portion 32 and including surfaces that are substantially perpendicular to the side portions 311. The lightening portion 31c holds a magnet 12 described below. A plane, of the movable part 3, passing through an end portion of the outer circumferential portion 31 where the magnet 12 is disposed (an end portion on the side of the lightening portion 31c) meets the magnet 12. Accordingly, the thickness of the movable-side sliding surfaces 31a of the movable part 3 in the radial direction may be made thicker compared with other portions, and the rigidity and the machining accuracy may be increased.

The movable part 3 holds the movable lens group Gv. More specifically, the inner circumferential portion 32 of the movable part 3 holds a first movable lens Lv1 of the movable lens group Gv.

The movable part 3 is inserted into the fixing part main body 20 with the movable-side sliding surfaces 31a contacting the fixing-side sliding surfaces 23. In the first embodiment, when the movable part 3 is moved closest to the object side, the object-side fixed lens group Gf is arranged near the movable lens group Gv of the movable part 3.

The movable part 3 having the configuration described above is formed by using a material such as stainless steel, aluminum or resin, for example.

As illustrated in FIG. 4, with the optical unit 1, a length L1 from the position, on the movable-side sliding surface 31a of the movable part 3, closest to the object side to the position closest to the image side, in the direction along the axis C, is greater than a length L2 from an emitting surface of the object-side fixed lens group Gf held by the front frame portion 4 to an incident surface of the image-side fixed lens group Gb held by the rear frame portion 5 (L1>L2). Additionally, the length from the position, on the movable-side sliding surface 31a of the movable part 3, closest to the object side to the position closest to the image side does not include chamfered portions.

Next, a configuration of the voice coil motor 10 will be described. As illustrated in FIG. 3, the voice coil motor 10 includes a coil 11 arranged on the fixing part main body 20 of the fixing part 2, and magnets 12 arranged on the movable part 3 in a manner facing the coil 11.

As illustrated in FIGS. 3 and 4, the coil 11 includes a first coil 11a wound around the outer circumference of the support portions 22 of the fixing part main body 20, and a second coil 11b arranged next to the first coil 11a in the axis C direction and wound around the outer circumference of the support portions 22 of the fixing part main body 20. Additionally, as the coil 11, a coil that is wound in advance may be disposed, or a coil may be directly wound around the support portions 22. The first coil 11a and the second coil 11b, which are adjacent to each other in the axis C direction, are desirably connected in series, but may alternatively be connected in parallel.

As illustrated in FIG. 3, the first coil 11a and the second coil 11b include planar portions 11ap and 11bp, which face the lightening portions 22a of the fixing part main body 20 (FIG. 3 illustrates the second coil 11b). Moreover, the first coil 11a and the second coil 11b include cylindrical portions 11at and 11bt, which face the support portions 22. The first coil 11a includes four planar portions 11ap and four cylindrical portions 11at, which are alternately arranged in a cross-section perpendicular to the axis C. In the same manner, the second coil 11b includes four planar portions 11bp and four cylindrical portions 11bt, which are alternately arranged in a cross-section perpendicular to the axis C (see FIG. 3).

As illustrated in FIGS. 2 to 4, as the magnet 12, there are two first magnets 12a and two second magnets 12b, the first magnet 12a and the second magnet 12b being arranged next to each other along the axis C direction, on the inside of the planar portion 11ap of the first coil 11a and the planar portion 11bp of the second coil 11b, while facing the planar portions 11ap and 11bp. The two magnets arranged next to each other along the axis C direction, i.e. the first magnet 12a (magnetic portion) and the second magnet 12b (second magnetic portion), are provided at each of positions that face each other in a cross-section perpendicular to the axis C. Additionally, the positions of the first magnets 12a, and of the second magnets 12b, may be positions that face each other with respect to the axis C; for example, an angle formed by two line segments connecting respective centers of the first magnets 12a, which face each other, and the axis C may be 180 degrees or may be other than 180 degrees.

As illustrated in FIG. 4, the total of widths of the first magnet 12a and the second magnet 12b in the axis C direction is shorter than the total of widths of the first coil 11a and the second coil 11b in the axis C direction. Accordingly, the first magnet 12a and the second magnet 12b may be caused to be constantly present within the widths of the first coil 11a and the second coil 11b in the axis C direction, in the movement range of the movable part 3.

Figure 7:
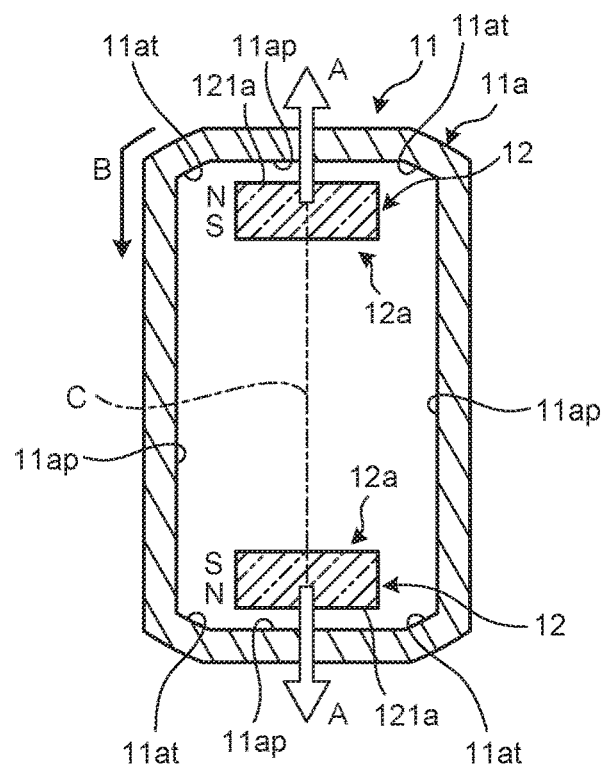
FIG. 7 is a diagram illustrating a configuration of only a voice coil motor, at a cross-section taken along a line II-II in FIG. 4.
Figure 8:
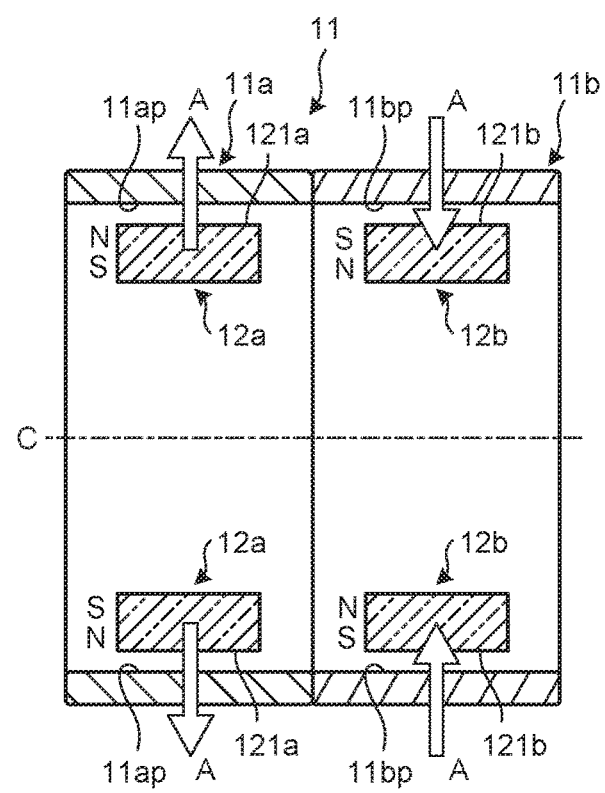
FIG. 8 is a diagram illustrating only the voice coil motor, at the same cross-section as FIG. 4.

FIG. 7 is a diagram illustrating a configuration of only the voice coil motor, at a cross-section taken along a line II-II in FIG. 4. FIG. 8 is a diagram illustrating only the voice coil motor, at the same cross-section as FIG. 4.

As illustrated in FIGS. 7 and 8, a set of first magnet 12a and second magnet 12b along the axis C direction are arranged with a space between the two magnets. A set of first magnets 12a, and a set of second magnets 12b are each magnetized in the radial direction, with the magnetic poles being opposite. In the case illustrated in FIGS. 7 and 8, the N poles of the first magnets 12a are on the first coil 11a side, and the S poles are on the opposite side, and the S poles of the second magnets 12b are on the second coil 11b side, and the N poles are on the opposite side. In this case, magnetic polarization directions of the first magnets 12a and the second magnets 12b are perpendicular to the axis C, as indicated by outlined arrows A illustrated in FIGS. 7 and 8.

Additionally, more generally, the magnetic polarization directions of the first magnets 12a and the second magnets 12b may be any directions as long as the directions intersect the axis C.

In the first embodiment, the winding direction of the coil 11 is desirably reversed between the set of first magnets 12a and the set of second magnets 12b. For example, in the case where the first coil 11a is wound in the direction of an arrow B, as illustrated in FIG. 7, the second coil 11b is wound in the opposite direction. Alternatively, the winding directions of the first coil 11a and the second coil 11b may be made the same, and the first coil 11a and the second coil 11b may be connected in such a way that the current directions are opposite. In this case, as illustrated in FIG. 7, current is to flow through the second coil 11b in a direction opposite the arrow B when current is caused to flow through the first coil 11a in the direction of the arrow B.

According to the optical unit 1 having the configuration described above, the movable part 3 is arranged radially inside the fixing part main body 20 around which the first coil 11a is wound, the movable part 3 installing the first magnets 12a such that the first magnets 12a face the first coil 11a. Accordingly, each planar portion 11ap of the first coil 11a is present within a magnetic field, the direction of which is perpendicular to a surface 121a of the corresponding first magnet 12a, the surface 121a being the outer side of the first magnet 12a in the radial direction. Additionally, the second magnet 12b is also configured in the same manner. Accordingly, the drive efficiency is increased, and the movable part 3 may be swiftly moved. Also, by making the surface 121a, which is the outer side of the first magnet 12a in the radial direction, and a surface 121b, which is the outer side of the second magnet 12b in the radial direction, planar surfaces, assembly of the optical unit 1 may be facilitated.

When current flows through the coil 11 of the optical unit 1, a force in the axis C direction is generated on the movable part 3 due to the influence of the magnetic field of the magnets 12, and the movable part 3 is moved in the axis C direction relative to the fixing part 2. For example, by controlling the current which is to flow through each of the first coil 11a and the second coil 11b, the movable part 3 may be moved relative to the fixing part 2. Also in the state where the movable part 3 is moving relative to the fixing part 2, the surfaces, of the magnets 12, which are on the outside in the radial direction are arranged within the lightening portions 22a of the fixing part main body 20.

Moreover, as illustrated in FIG. 4, according to the optical unit 1, the outer circumferential surface of the movable part 3 forms the movable-side sliding surfaces 31a, which contact the fixing-side sliding surfaces 23 of the fixing part main body 20. By causing the fixing-side sliding surfaces 23 of the fixing part main body 20 to contact the movable-side sliding surfaces 31a of the movable part 3, the movable part 3 may be moved while being constantly in contact with the fixing part main body 20, and tilting of the movable part 3 relative to the fixing part 2 may be suppressed, and thus, the movable part 3 may be accurately moved.

Figure 9:
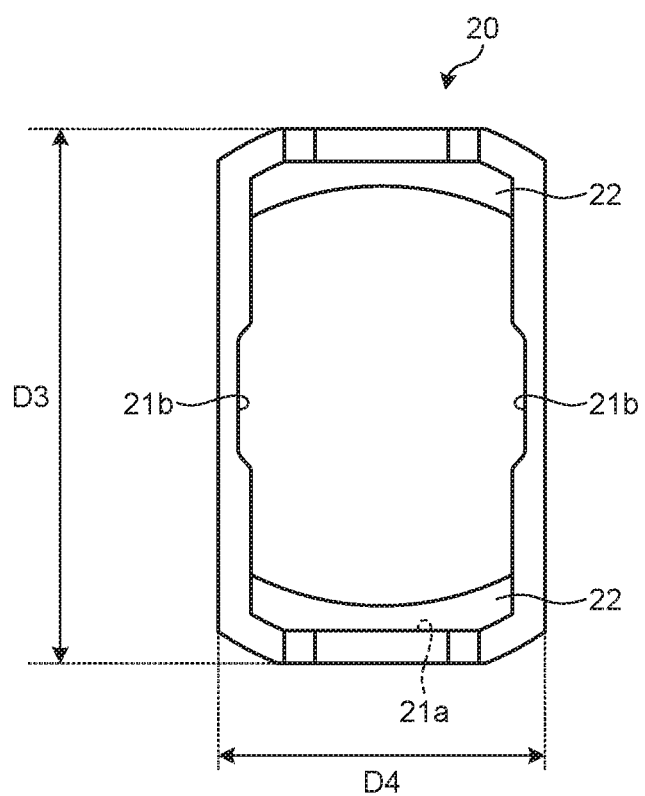
FIG. 9 is a plan view illustrating a configuration of the fixing part main body of the optical unit according to the first embodiment.

FIG. 9 is a plan view illustrating a configuration of the fixing part main body of the optical unit according to the first embodiment, and is a diagram illustrating the cylindrical portion 21 seen along the axis C direction from the object side. In the first embodiment, as illustrated in FIG. 1, a maximum dimension D1, of the first distal end portion 43, in the magnetization direction of the magnets 12 (the facing direction of the magnets 12: first direction) is greater than a maximum dimension D2, of the first distal end portion 43, in a direction (second direction) perpendicular to the magnetization direction and the axis C direction. Also, as illustrated in FIG. 9, a maximum dimension D3, of the cylindrical portion 21 of the fixing part main body 20, in the magnetization direction of the magnets 12 is greater than a maximum dimension D4, of the cylindrical portion 21, in the direction perpendicular to the magnetization direction and the axis C direction. Additionally, because the coil 11 (first coil 11a and second coil 11b) is wound around the support portions 22, a maximum dimension, of the shape formed by winding (shape seen from the axis C direction), in the magnetization direction of the magnets 12 is greater than a maximum dimension, of the shape, in the direction perpendicular to the magnetization direction and the axis C direction.

The ratio of the maximum dimension D2 to the maximum dimension D1 (D2/D1) is desirably 0.4≤(D2/D1)≤0.8, and more desirably, 0.5≤(D2/D1)≤0.7. Likewise, the ratio of the maximum dimension D4 to the maximum dimension D3 (D4/D3) is desirably 0.4≤(D4/D3)≤0.8, and more desirably, 0.5≤(D4/D3)≤0.7. As described above, the optical unit 1 according to the first embodiment has an oval shape when seen in a plan view from the axis C direction. Moreover, it is desirable that the movable part 3, the second distal end portion 44, and the rear frame portion 5 each have an oval shape (in plan view) when seen in the axis C direction (center axis direction of each member), with the maximum dimension in the magnetization direction of the magnets 12 being greater than the maximum dimension in the direction perpendicular to the magnetization direction and the axis C direction. With the optical unit 1, it is sufficient if the shape of at least the outer circumference of the cylindrical portion 21 of the fixing part main body 20 (shape of the outer circumference seen from the axis C direction) is oval. In this case, structural elements other than the fixing part main body 20 do not have to be oval, as long as the elements have shapes that allow the elements to be attached to one another.

According to the first embodiment described above, the voice coil motor 10 is provided, the voice coil motor 10 including the coil 11 arranged on the fixing part 2 and the magnets 12 arranged on the movable part 3 and magnetically polarized in the direction perpendicular to the axis C, where the voice coil motor 10 is capable of moving the movable part 3 relative to the fixing part 2 along the axis C direction, and thus, the drive efficiency is increased, and the movable part 3 may be swiftly moved. Moreover, also during operation of the movable part 3, the fixing-side sliding surfaces 23 of the fixing part main body 20 and the movable-side sliding surfaces 31a of the movable part 3 come into contact, and thus, tilting of the movable part 3 relative to the fixing part 2 may be suppressed, and the movable part 3 may be accurately moved. Accordingly, reduction in the size and the weight of the actuator for moving a movable lens may be realized.

Also, according to the first embodiment, the fixing-side sliding surfaces 23 are provided on the radially inner side (inner circumferential surface) of the fixing part main body 20, and the movable part 3 is provided on the radially inner side of the fixing part 2 (fixing part main body 20), and thus, miniaturization in the radial direction may be realized.

Also, according to the first embodiment, because the center axis of the fixing part 2 and the center axis of the movable part 3 each coincide with the axis C, and the fixing part 2 and the movable part 3 have the same center axis, tilting of the movable part 3 relative to the fixing part 2 may be suppressed. Accordingly, driving of the optical unit 1 may be stabilized, and miniaturization in the radial direction may be realized.

Also, according to the first embodiment, the optical unit 1 is oval when seen in a plan view from the axis C direction, and thus, miniaturization in the radial direction, or more specifically, in the direction perpendicular to the facing direction of the two sets of magnets 12, may be realized.

Also, according to the first embodiment, the magnets 12 are disposed in the lightening portions 31c of the movable part 3, and miniaturization in the facing direction of the two sets of magnets 12 may be realized.

Moreover, according to the first embodiment, the fixing part 2 is configured from the fixing part main body 20, the front frame portion 4, and the rear frame portion 5, and thus, the number of components and the assembly steps are reduced and the degree of freedom in design is increased, and the cost may be reduced.

Moreover, according to the first embodiment, with the optical unit 1, the length L1 from the position, on the movable-side sliding surface 31a of the movable part 3, closest to the object side to the position closest to the image side, in the direction along the axis C, is greater than the length L2 from the emitting surface of the object-side fixed lens group Gf held by the front frame portion 4 to the incident surface of the image-side fixed lens group Gb held by the rear frame portion 5, and thus, tilting of the movable part 3 relative to the fixing part 2 may be suppressed. Accordingly, driving of the optical unit 1 may be stabilized, and also, miniaturization in the axis direction may be realized.

Moreover, according to the first embodiment, because the coil 11 is wound around the axis C, the sliding axis of the movable part 3 and the acting axis of thrust generated by the voice coil motor 10 may be made the same, and stable driving may be achieved.

Moreover, according to the first embodiment, because the fixing-side sliding surface 23 of the fixing part 2 is formed while being divided in the circumferential direction, the optical unit 1 may be miniaturized by a simple structure.

Moreover, according to the first embodiment, the fixing part main body 20 has a shape that is divided in the circumferential direction on one end side in the axis C direction, and also holds the front frame portion 4. This allows the rigidity of the fixing part 2 to be increased without increasing the size in the radial direction. Also, when the one end side of the fixing part main body 20 holds the front frame portion 4 while being in close contact with the front frame portion 4, the shape of end portions of the support portions 22, on a side different from the side continuous to the cylindrical portion 21, becomes fixed, and the shape of the fixing-side sliding surfaces 23 may be stabilized. Accordingly, driving of the optical unit 1 may be stabilized, and also, miniaturization in the radial direction may be realized.

Moreover, according to the first embodiment, a plurality of magnets 12 are symmetrically arranged with respect to the axis C, and thus, a driving force may be stably increased.

Moreover, according to the first embodiment, the magnets 12 include a plurality of sets of first magnet 12a and second magnet 12b, where the first magnet 12a and the second magnet 12b are arranged next to each other in the axis C direction and have opposite magnetic polarization directions and where a plurality of first magnets 12a have the same magnetic polarization direction, and the coil 11 includes the first coil 11a facing the plurality of first magnets 12a and a second coil 11b facing a plurality of second magnets 12b connected to the first coil 11a, and the direction of flow of current is opposite for the first coil 11a and the second coil 11b, and thus, the driving force may be increased.

Second Embodiment

Figure 10:
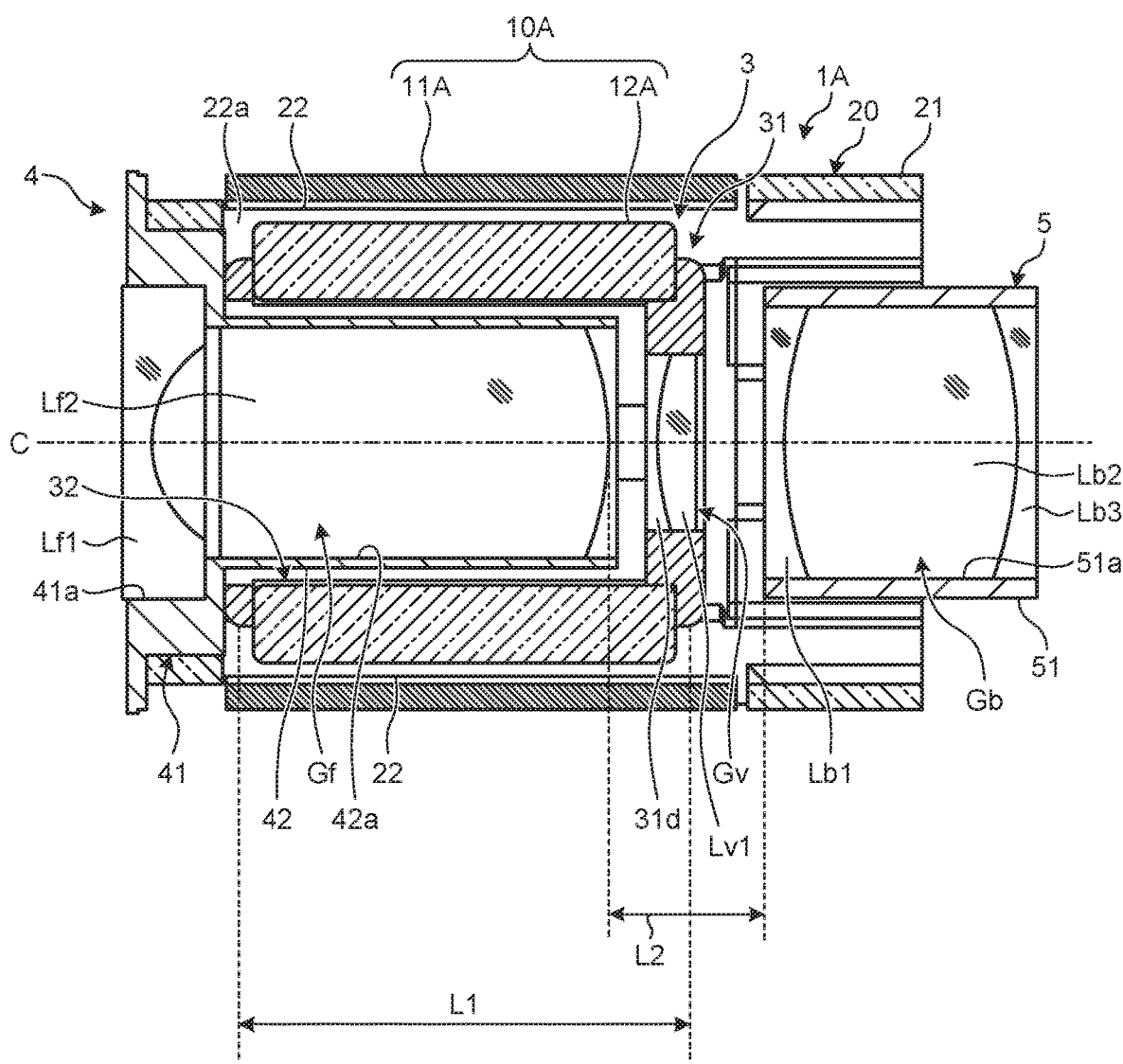
FIG. 10 is a diagram illustrating a configuration of an optical unit according to a second embodiment.

FIG. 10 is a diagram illustrating a configuration of an optical unit according to a second embodiment, and is a cross-sectional view of the optical unit at a cross-section taken along the line I-I in FIG. 3. Additionally, structural elements the same as those of the configuration described above are denoted by the same reference signs. The first embodiment describes a case where the first coil 11a and the second coil 11b, which are next to each other in the axis C direction and the winding directions of which are different from each other, and two sets of first magnet 12a and second magnet 12b are provided, but there may be one or three or more sets of magnets (magnetic portions). The second embodiment describes an example where one set of magnets is provided. An optical unit 1A illustrated in FIG. 10 includes the fixing part 2, the movable part 3 capable of moving relative to the fixing part 2, and a voice coil motor 10A for generating a driving force for moving the movable part 3 relative to the fixing part 2.

As illustrated in FIG. 10, the voice coil motor 10A includes a coil 11A arranged on the fixing part main body 20 of the fixing part 2, and magnets 12A arranged on the movable part 3 in a manner facing the coil 11A.

As illustrated in FIG. 10, the coil 11A is a coil that is wound on the outer circumference of the support portions 22 of the fixing part main body 20 along a predetermined direction. Additionally, as the coil 11A, a coil that is wound in advance may be disposed, or a coil may be directly wound around the support portions 22. The coil has the same shape as the first coil 11a and the second coil 11b described above (with respect to the shape seen from the axis C direction, and the like) except for the number of windings.

As illustrated in FIG. 10, the magnets 12A are a pair of magnets which are on the inside of the coil 11A and which face planar portions of the coil 11A. The pair of magnets 12A (magnetic portions) are disposed at positions facing each other in a cross-section perpendicular to the axis C. Additionally, in the second embodiment, the magnets 12A are installed at positions facing each other with respect to the axis C, but the magnets 12A may alternatively be installed at an angle other than 180 degrees.

As illustrated in FIG. 10, the width of the magnets 12A in the axis C direction is shorter than the width of the coil 11A in the axis C direction. Accordingly, the magnets 12A may be caused to be constantly present within the width of the coil 11A in the axis C direction, in the movement range of the movable part 3.

As illustrated in FIG. 10, with the optical unit 1A, the length L1 from the position, on the movable-side sliding surface 31a of the movable part 3, closest to the object side to the position closest to the image side, in the direction along the axis C, is greater, as in the first embodiment, than the length L2 from the emitting surface of the object-side fixed lens group Gf held by the front frame portion 4 to the incident surface of the image-side fixed lens group Gb held by the rear frame portion 5 (L1>L2).

Third Embodiment

Figure 11:
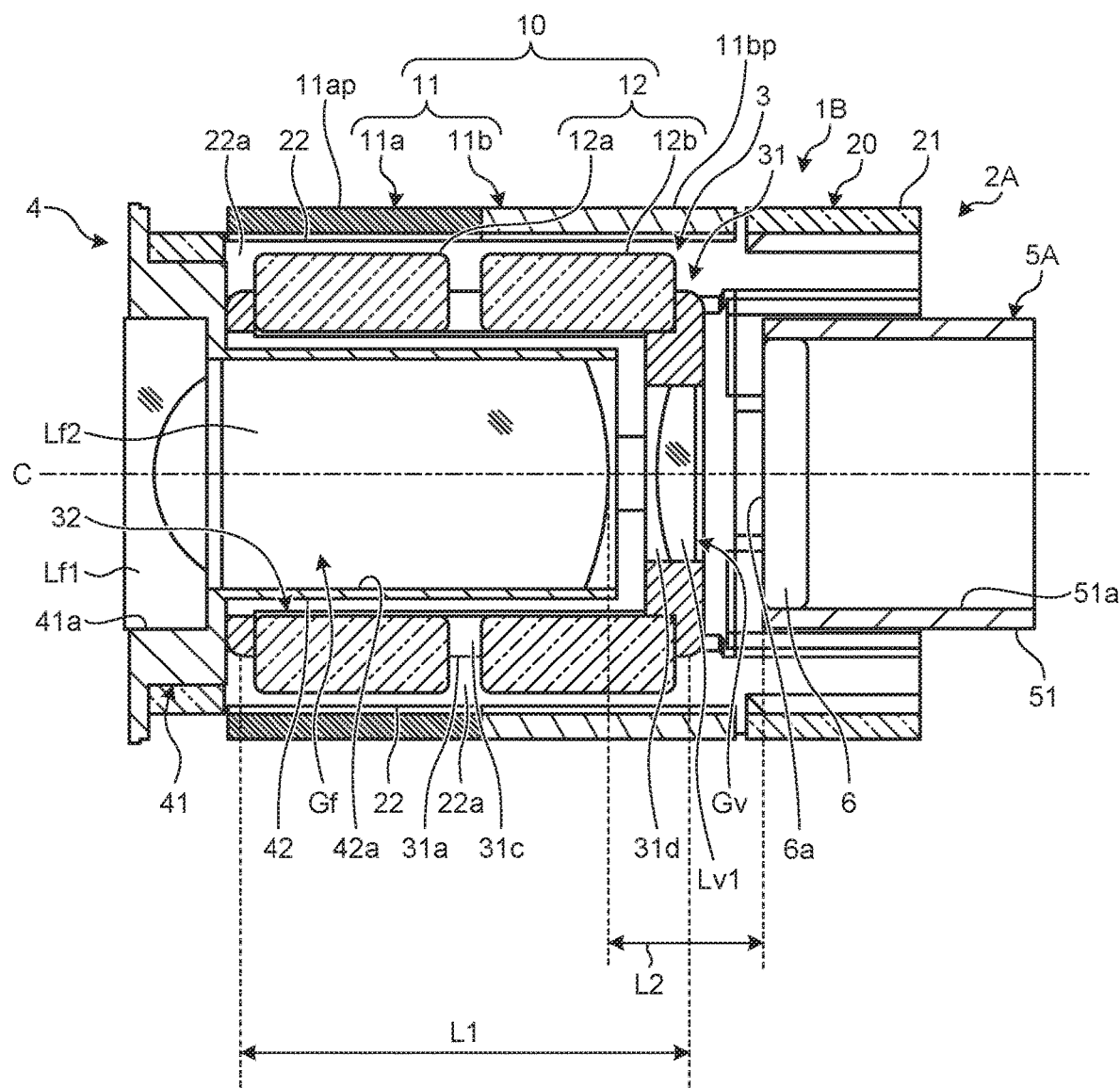
FIG. 11 is a diagram illustrating a configuration of an optical unit according to a third embodiment.

FIG. 11 is a diagram illustrating a configuration of an optical unit according to a third embodiment, and is a cross-sectional view of the optical unit at a cross-section taken along the line I-I in FIG. 3. Additionally, structural elements the same as those of the configuration described above are denoted by the same reference signs. An optical unit 1B illustrated in FIG. 11 includes a fixing part 2A, the movable part 3 capable of moving relative to the fixing part 2A, and the voice coil motor 10 for generating a driving force for moving the movable part 3 relative to the fixing part 2A.

The fixing part 2A includes the fixing part main body 20, the front frame portion 4, and a rear frame portion 5A for holding an image sensor 6, the rear frame portion 5A being attached to the image side of the fixing part main body 20. The image sensor 6 is configured by a CCD (Charge Coupled Device) or a CMOS (Complementary Metal Oxide Semiconductor), and receives light transmitted through the movable lens group Gv and performs a photoelectric conversion process.

As illustrated in FIG. 11, with the optical unit 1B, a length L3 from the position, on the movable-side sliding surface 31a of the movable part 3, closest to the object side to the position closest to the image side, in the direction along the axis C, is greater than a length L4 from the emitting surface of the object-side fixed lens group Gf held by the front frame portion 4 to a light receiving surface 6a of the image sensor 6 held by the rear frame portion 5A (L3>L4).

Fourth Embodiment

Figure 12:
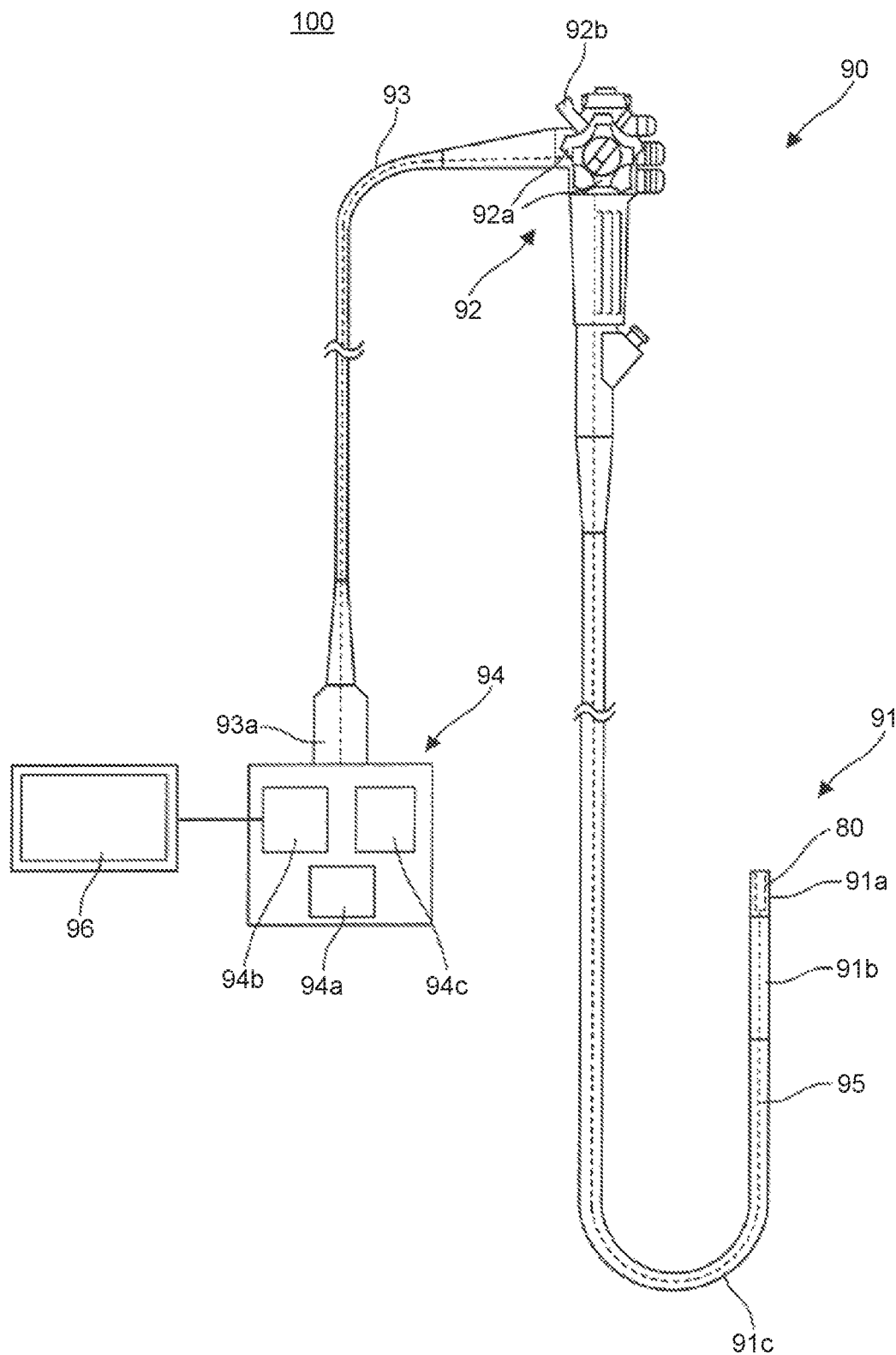
FIG. 12 is a diagram illustrating a configuration of an endoscope system provided with an endoscope according to a fourth embodiment.

FIG. 12 is a diagram illustrating a configuration of an endoscope system provided with an endoscope according to a fourth embodiment. An endoscope system 100 illustrated in the drawing includes an endoscope 90, a control device 94, and a display device 96. The endoscope 90 includes the optical unit 1 according to the first embodiment described above, or the optical unit 1A or 1B.

The endoscope 90 may be introduced into a subject such as a human body, and optically captures a predetermined observed region inside the subject. Additionally, the subject into which the endoscope 90 is to be introduced is not limited to a human body, and may be another living body or an artificial material such as a machine or a building. In other words, the endoscope 90 may be a medical endoscope or an industrial endoscope.

The endoscope 90 includes an insertion unit 91 to be introduced into a subject, an operating unit 92 positioned at a proximal end of the insertion unit 91, and a universal cord 93 as a composite cable extending from the operating unit 92.

The insertion unit 91 includes a distal end portion 91a disposed at a distal end, a freely bendable bending portion 91b disposed on the proximal end side of the distal end portion 91a, and a flexible tube portion 91c disposed on the proximal end side of the bending portion 91b and connected to the distal end side of the operating unit 92, the flexible tube portion 91c having flexibility. An imaging unit 80 for condensing light from a subject and for capturing an image of the subject is provided at the distal end portion 91a. The imaging unit 80 includes the optical unit 1 or 1A for condensing light from a subject, and an image sensor for photoelectrically converting, and outputting, light condensed by the optical unit 1 or 1A. Additionally, in the case of using the optical unit 1B, the image sensor 6 is provided inside the optical unit 1B. The image sensor is configured by a CCD or a CMOS. Additionally, the endoscope 90 may be a rigid endoscope where the insertion unit 91 does not include the flexible tube portion 91c.

The operating unit 92 includes an angle operating unit 92a used for operating a bending state of the bending portion 91b, and a zoom operating unit 92b for issuing an instruction regarding operation of the voice coil motor 10 and for performing zoom operation of the optical unit 1. The angle operating unit 92a is knob-shaped, and the zoom operating unit 92b is lever-shaped, but each unit may take another form such as a volume switch or a push switch.

The universal cord 93 is a member for connecting the operating unit 92 and the control device 94. The endoscope 90 is connected to the control device 94 via a connector 93a provided at a proximal end portion of the universal cord 93.

Cables 95, such as a wire, an electric wire and an optical fiber, are inserted through the insertion unit 91, the operating unit 92 and the universal cord 93.

The control device 94 includes a drive controller 94a for controlling the bending state of the bending portion 91b, an image controller 94b for controlling the imaging unit 80, and a light source controller 94c for controlling a light source device not illustrated. The control device 94 includes a processor such as a CPU (Central Processing Unit), and controls the entire endoscope system 100 in an overall manner.

The drive controller 94a includes an actuator, and is mechanically connected to the operating unit 92 and the bending portion 91b by a wire. The drive controller 94a controls the bending state of the bending portion 91b by causing the wire to move forward or backward.

The image controller 94b is electrically connected to the imaging unit 80 and the operating unit 92 by an electric wire. The image controller 94b performs driving control of the voice coil motor 10 or 10A provided in the imaging unit 80, and performs processing of an image captured by the imaging unit 80. An image processed by the image controller 94b is displayed by the display device 96.

The light source controller 94c is optically connected to a light source and the operating unit 92 by an optical fiber. The light source controller 94c controls brightness and the like of light radiated from the distal end portion 91a.

Additionally, the operating unit 92 may be formed separately from the insertion unit 91, and operation of the insertion unit 91 may be performed by remote operation.

The endoscope system 100 having the configuration described above includes the imaging unit 80 including the optical unit 1, 1A or 1B, and thus, the endoscope system 100 is small and zooming may be swiftly changed, and application to video capturing may be suitably performed.

Furthermore, the optical unit 1, 1A or 1B of the endoscope system 100 is oval when seen in a plan view from the axis C direction, and thus, miniaturization in the radial direction, or more specifically, in the direction perpendicular to the facing direction of the two sets of magnets 12, may be realized and the diameter of the imaging unit 80 may be reduced.

Moreover, according to the endoscope system 100, the magnets 12 are provided at the movable part 3 and the coil 11 is provided at the fixing part 2, and thus, a cable connected to the coil 11 does not have to be moved. Accordingly, the cable is not moved in a limited space in the distal end portion of the endoscope 90 and is thus not broken, and high durability is achieved.

OTHER EMBODIMENTS

Heretofore, modes for carrying out the present disclosure have been described, but the present disclosure is not limited by the embodiments described above. For example, the optical unit 1 may further include at least one magnetic detector for detecting magnetism, and a current controller for controlling current that flows through the coil 11, based on a detection result of the magnetic detector. The magnetic detector is realized by using a Hall element or a magneto resistive sensor (MR sensor), for example. The magnetic detector is fixedly installed to a support member that is provided on a radially outer circumferential side of the coil 11. By controlling current that flows through the coil 11 based on the magnetism detected by the magnetic detector, the driving speed and the stop position of the movable part 3 may be more accurately controlled.

Also, the number of magnets disposed on the movable part does not have to be the number described in the first embodiment.

Furthermore, the lightening portions provided at the fixing part does not have to penetrate to the radially outer circumferential side as long as the lightening portions allow attachment of the magnets.

As described above, the present disclosure may include various embodiments not described herein, and the design may be changed as appropriate within the scope of the technical idea described in the claims.

According to the present embodiment, the size and the weight of an actuator for moving a movable lens forward or backward may be reduced.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical unit comprising:
    a fixing part including:
        a front frame configured to hold an object-side fixed lens group;
        a rear frame configured to hold one of an image-side fixed lens group or an image sensor; and
        a fixing part main body configured to hold the front frame and the rear frame;
    a movable body configured to hold a movable lens group between the object-side fixed lens group and the image-side fixed lens group or the image sensor, the movable body being arranged, slidably relative to the fixing part main body, on a radially inner side of the fixing part main body; and
    a voice coil motor including:
        a magnetic portion arranged at the movable body, the magnetic portion being magnetically polarized in a direction intersecting an optical axis of the object-side fixed lens group, and
        a coil arranged at the fixing part main body and positioned on a radially outer side of the fixing part main body with respect to the magnetic portion, the voice coil motor being configured to move the movable body relative to the fixing part main body along a direction of the optical axis, wherein
    a maximum dimension of the fixing part main body in a first direction parallel to a magnetization direction of the magnetic portion is greater than a maximum dimension of the fixing part main body in a second direction perpendicular to the first direction and the direction of the optical axis; and
    a length from a position, on a movable-side sliding surface of the movable body, closest to an object side to a position closest to an image side, in the direction along the optical axis, is greater than a length from an emitting surface of the object-side fixed lens group held by the fixing part to an incident surface of the image-side fixed lens group or a light receiving surface of the image sensor.

2. The optical unit according to claim 1, wherein
    the coil is wound around the optical axis, and
    a maximum dimension of the coil in the first direction is greater than a maximum dimension of the coil in the second direction.

3. The optical unit according to claim 1, wherein a maximum dimension of the front frame in the first direction is greater than a maximum dimension of the front frame in the second direction.

4. The optical unit according to claim 1, wherein a maximum dimension of the rear frame in the first direction is greater than a maximum dimension of the rear frame in the second direction.

5. The optical unit according to claim 1, wherein a maximum dimension in the first direction is greater than a maximum dimension in the second direction with respect to a shape seen from the direction of the optical axis.

6. The optical unit according to claim 1, wherein a maximum dimension of the movable body in the first direction is greater than a maximum dimension of the movable body in the second direction.

7. The optical unit according to claim 1, wherein
    the fixing part main body includes
        a cylindrical portion having a cylindrical shape, and
        a support portion extending from the cylindrical portion along the optical axis, the support portion supporting the coil, and
    the fixing part is divided in a circumferential direction on one end side in the direction of the optical axis, and holds the front frame and the rear frame by the one end side and another end side.

8. The optical unit according to claim 7, wherein a lightening portion is at least formed at a part of the support portion.

9. The optical unit according to claim 1, wherein the movable body includes a cut-out portion formed by cutting out the movable body from one end along the optical axis.

10. The optical unit according to claim 1, wherein a plane passing through an end portion of a movable-side sliding surface of the movable body part, on a side where the magnetic portion is arranged, intersects the magnetic portion.

11. The optical unit according to claim 1, wherein
    the magnetic portion includes two magnets that are arranged at positions facing each other in the first direction, and
    the coil is a coil facing each magnet of the magnetic portion.

12. The optical unit according to claim 11, further comprising:
    a second magnetic portion that is adjacent along the optical axis, with an opposite magnetic polarization direction from a magnetic polarization direction of the magnetic portion; and
    a second coil facing each magnet of the second magnetic portion and connected to the coil, wherein
    two magnets of the magnetic portion have a same magnetic polarization direction with respect to the optical axis,
    two magnets of the second magnetic portion have a same magnetic polarization direction with respect to the optical axis, and
    a direction of flow of current is opposite between the coil and the second coil.

13. The optical unit according to claim 1, wherein a ratio of the maximum dimension in the second direction to the maximum dimension in the first direction is between 0.4 and 0.8, inclusive.

14. An endoscope adapted to be inserted inside a subject for observation of the inside of the subject, the endoscope comprising:
the optical unit according to claim 1; and
the image sensor, the image sensor being configured to convert light condensed by the optical unit into an electrical signal.

15. An optical unit comprising:
a fixing part including:
a front frame configured to hold an object-side fixed lens group;
a rear frame configured to hold one of an image-side fixed lens group or an image sensor; and
a fixing part main body configured to hold the front frame and the rear frame;
a movable body configured to hold a movable lens group between the object-side fixed lens group and the image-side fixed lens group or the image sensor, the movable body being arranged, slidably relative to the fixing part main body, on a radially inner side of the fixing part main body; and
a voice coil motor including:
a magnetic portion arranged at the movable body, the magnetic portion being magnetically polarized in a direction intersecting an optical axis of the object-side fixed lens group, and
a coil arranged at the fixing part main body and positioned on a radially outer side of the fixing part main body with respect to the magnetic portion, the voice coil motor being configured to move the movable body relative to the fixing part main body along a direction of the optical axis, wherein
a maximum dimension of the fixing part main body in a first direction parallel to a magnetization direction of the magnetic portion is greater than a maximum dimension of the fixing part main body in a second direction perpendicular to the first direction and the direction of the optical axis;
the fixing part main body includes
a cylindrical portion having a cylindrical shape, and
a support portion extending from the cylindrical portion along the optical axis, the support portion supporting the coil, and
the fixing part is divided in a circumferential direction on one end side in the direction of the optical axis, and holds the front frame and the rear frame by the one end side and another end side.

16. The optical unit according to claim 15, wherein a lightening portion is at least formed at a part of the support portion.

17. An optical unit comprising:
a fixing part including:
a front frame configured to hold an object-side fixed lens group;
a rear frame configured to hold one of an image-side fixed lens group or an image sensor; and
a fixing part main body configured to hold the front frame and the rear frame;
a movable body configured to hold a movable lens group between the object-side fixed lens group and the image-side fixed lens group or the image sensor, the movable body being arranged, slidably relative to the fixing part main body, on a radially inner side of the fixing part main body; and
a voice coil motor including:
a magnetic portion arranged at the movable body, the magnetic portion being magnetically polarized in a direction intersecting an optical axis of the object-side fixed lens group, and
a coil arranged at the fixing part main body and positioned on a radially outer side of the fixing part main body with respect to the magnetic portion, the voice coil motor being configured to move the movable body relative to the fixing part main body along a direction of the optical axis, wherein
a maximum dimension of the fixing part main body in a first direction parallel to a magnetization direction of the magnetic portion is greater than a maximum dimension of the fixing part main body in a second direction perpendicular to the first direction and the direction of the optical axis; and
a plane passing through an end portion of a movable-side sliding surface of the movable body, on a side where the magnetic portion is arranged, intersects the magnetic portion.

* * * * *